United States Patent
Vainshelboim et al.

(10) Patent No.: US 7,871,377 B2
(45) Date of Patent: Jan. 18, 2011

(54) METHOD OF EVALUATING HUMAN SUBCONSCIOUS RESPONSE TO SMELL

(75) Inventors: Alex Vainshelboim, Maple Grove, MN (US); Konstantin Korotkov, St. Petersberg (RU); Peter Matravers, Minnetonka, MN (US); Michael Hayes, Centerville, MN (US); Kenneth Momoh, St. Paul, MN (US)

(73) Assignee: Aveda Corporation, Blaine, MN (US)

( * ) Notice: Subject to any disclaimer, the term of this patent is extended or adjusted under 35 U.S.C. 154(b) by 1283 days.

(21) Appl. No.: 11/336,579

(22) Filed: Jan. 20, 2006

(65) Prior Publication Data

US 2006/0266371 A1    Nov. 30, 2006

Related U.S. Application Data

(60) Provisional application No. 60/645,904, filed on Jan. 21, 2005.

(51) Int. Cl.
*A61B 5/08* (2006.01)
*A61B 5/05* (2006.01)
*A61B 13/00* (2006.01)
*A61B 5/00* (2006.01)

(52) U.S. Cl. .................. 600/303; 600/547; 600/407; 600/558; 600/559; 600/300

(58) Field of Classification Search ................ 600/300, 600/301, 303, 547, 548, 552–555, 557–559
See application file for complete search history.

(56) References Cited

U.S. PATENT DOCUMENTS

| | | | | |
|---|---|---|---|---|
| 4,195,641 A * | 4/1980 | Joines et al. | ............... | 600/346 |
| 4,222,658 A * | 9/1980 | Mandel | ..................... | 396/14 |
| 4,386,834 A * | 6/1983 | Toolan | ..................... | 396/661 |
| 4,542,969 A * | 9/1985 | Omura | ..................... | 396/661 |
| 4,679,924 A * | 7/1987 | Wamsley | ..................... | 396/14 |
| 5,208,453 A * | 5/1993 | Hostetler | .............. | 250/214 LA |
| 6,013,021 A * | 1/2000 | Lee | .............................. | 600/9 |
| 6,016,450 A | 1/2000 | Crock | | |
| 6,466,688 B1 | 10/2002 | Ramstack | | |
| 6,623,511 B1 | 9/2003 | Daffer et al. | | |
| 6,641,540 B2 * | 11/2003 | Fleischman et al. | ......... | 600/459 |
| 6,746,397 B2 | 6/2004 | Lee et al. | | |
| 2002/0077551 A1 * | 6/2002 | Fleischman et al. | ......... | 600/459 |

(Continued)

FOREIGN PATENT DOCUMENTS

RU       2110824       5/1998

(Continued)

OTHER PUBLICATIONS

PCT International Search Report; International Application No. PCT/US06/02362; Completion Date: Apr. 30, 2007; Date of Mailing: Aug. 8, 2007.

(Continued)

*Primary Examiner*—Charles A Marmor, II
*Assistant Examiner*—Navin Natnithithadha
(74) *Attorney, Agent, or Firm*—Cynthia R. Miller; Radha Masilamani

(57) ABSTRACT

The present invention provides a method of evaluating the human subconscious response to smell and a method of evaluating a subject's subconscious response to an aroma stimulus.

13 Claims, 16 Drawing Sheets

U.S. PATENT DOCUMENTS

| | | | |
|---|---|---|---|
| 2003/0206834 A1* | 11/2003 | Chiao et al. | 422/124 |
| 2004/0068181 A1* | 4/2004 | Takeyama | 600/425 |
| 2004/0241186 A1 | 12/2004 | Huang | |
| 2006/0266371 A1* | 11/2006 | Vainshelboim et al. | 128/898 |

FOREIGN PATENT DOCUMENTS

| | | |
|---|---|---|
| RU | 2141250 | 11/1999 |
| RU | 2210982 | 8/2003 |
| RU | 2217047 | 11/2003 |
| RU | 2234854 | 8/2004 |
| SU | 1241181 | 6/1986 |
| SU | 1377813 | 2/1988 |
| SU | 1561066 | 4/1990 |
| SU | 1664286 | 7/1991 |
| WO | WO 99/27417 | 6/1999 |
| WO | WO 2004/075752 A1 | 9/2004 |
| WO | WO 2006/057568 | 6/2006 |
| WO | WO 2006/078190 A1 | 7/2006 |

OTHER PUBLICATIONS

PCT Written Opinion of the International Searching Authority, or the Declaration; International Application No. PCT/US06/02362; Completion Date: Apr. 30, 2007; Mailing Date: Aug. 8, 2007.

"Measuring Energy Fields, State of the Science" by Dr. Konstantin Korotkov, GDV Bioelectrography Series, vol. 1, 2004, pp. 13-16.

"Aura and Consciousness" by Dr. Konstantin Korotkov, 1998 (Book).

"Human Energy Field: Study with GDV Bioelectrography" by Dr. Konstantin Korotkov, 2002, pp. 21-25, 43-47, 270-273, 281, and 301-305.

Skarja et al., Influence of Ionic Composition of Water on the Corona Discharge Around Water Drops, Journal of Applied Physics, vol. 84, No. 5, pp. 3334-3338 (Sep. 1, 1998).

Korotkov et al., *Concentration Dependence of Gas Discharge Around Drops of Inorganic Electrolytes*, Journal of Applied Physics, vol. 89, pp. 4732-4736 (2001).

Krotkov et al., *Assessing Biophysicla Energy Transfer Mechanisms in Living Systems: The Basis of Life Process*, Journal of Alternative 7 Complementary Medicine, vol. 10, No. 1, pp. 49-57 (Feb. 2004).

"Color and Crystals: A Journey Through the Chakras" by Joy Gardner Gordon, Crossing Press; Freedom, California 95019, 1988 (Book).

B.H. Yoo et al., *Investigation of Jewelry Powders Radiating Far-Infrared Rays and the Biological Effects on Human Skin*, Journal of Cosmetic Science, vol. 53, pp. 175-184 (2002).

I.R. Bell et al., *Gas Discharge Visualization Evaluation of Ultramolecular Doses of Homeopathic Medicines Under Blinded, Controlled Conditions*, Journal of Alternative & Complementary Medicine, vol. 9, No. 1, pp. 25-38 (Feb. 2003).

M. Skarja et al., Journal of Applied Physics, vol. 84, p. 2436 (1998).

H. Odagiri-Shimizu et al., *Experimental Analysis of the Human Perception Threshold of a DC Electric Field*, Medical & Biological Engineering & Computing, vol. 37, pp. 727-732 (1999).

S.M. Roney-Dougal, *On a Possible Psychophysiology of the Yogic Chakra System* (on-line), available at www.psi-researchcentre.co.uk/article_2.html and downloaded on Jun. 7, 2006.

Korotkov, E., et al.; Journal of Applied Physics; Time dynamics of the gas discharge around drops of liquids; vol. 95; No. 7; pp. 3334-3338; Apr. 2004.

* cited by examiner

METHOD OF EVALUATING HUMAN SUBCONSCIOUS RESPONSE TO SMELL

We claim priority of provisional application 60/645,904, filed Jan. 21, 2005.

FIELD OF THE INVENTION

The present invention relates to a method of diagnosing human subconscious response to smell. In particular, the present invention relates to a non-invasive, subjective method of diagnosing human subconscious state based on subconscious response to smell.

BACKGROUND OF THE INVENTION

Recently, science has shifted more and more towards biophysics as Western medicine has proven inadequate. The biophysical view of life focuses on the matrix of energy and information. Although the dynamics of these are very complex and often difficult to measure, work in this area is yielding insights into a more subtle dimension of life.

Many lines of scientific and clinical evidence show that extremely small energetic stimuli to injured or sick organisms can promote healing. See "Scientific Analysis of the Human Aura," Rubik B., *Measuring Energy Fields, State of the Science*, Dr. Konstantin Korotkov, GDV Bioelectrography Series, vol. 1, 2004. For example, certain "energy medicines" such as homeopathy, biofield therapies, acupuncture and bioelectromagnetic therapies demonstrate that tiny nudges, repeated over time, can shift the dynamics of the organism, nudging it into a healing state. Id. These techniques are distinctly different from the approach of conventional medicine, which focuses on modifying the structure and/or biochemistry of life.

Virtually every indigenous culture has the belief in a vital force or life energy, known as vitalism. For example, there is the concept of qi in China, ki in Japan, prana in India, and so forth. It is possible that all of the indigenous systems of medicine were founded on the principal of vital force, and many of these medical systems remain outside of mainstream Western medicine today. However, vitalistic principles are key to many contemporary alternative systems of medicine, including homeopathy, chiropractry, Oriental medicine, Ayurvedic medicine, Anthroposophical medicine, and others.

Recently, studies have been performed using electronic technology to study energy field patterns of humans. Methods include electrodermal testing, which measures the flow of electricity at acupuncture points considered to correspond to the flow of energy along acupuncture meridians; thermography that maps the thermal patterns of the body; and EEG, ECG, and other similar clinical diagnostics which measure the electrical emission from key organs such as brain and heart, respectively, although belief is that this energy is simply waste. Scientists have also measured biophotons, the ultraweak light emitted from the body. Dowsing, psychic reading, and other subjective measures have also been used to assess the subtle energies of life.

However, there still remains a need to not only visualize part of the human biofield, but also to use that visualized image to diagnose the human in response to various stimuli.

SUMMARY OF THE INVENTION

The present invention provides a method of evaluating the human subconscious response to smell comprising the steps of (a) evaluating a subject's biofield showing the subject's individual energy fields as a biophysical construction, (b) determining a baseline relative balance of the subject's energy fields against a defined standard for energy fields, (c) exposing the subject to at least one aroma stimulus, and (d) redetermining the baseline relative balance of the subject's energy fields against the defined standard for energy fields.

The present invention further provides a method of evaluating a subject's subconscious response to an aroma stimulus comprising the steps of (a) evaluating the subject's corona discharge, (b) exposing the subject to an external stimulus, (c) re-evaluating the subject's corona discharge during the exposure step (b), and (d) finally evaluating the subject's corona discharge after exposure to the external stimulus.

DETAILED DESCRIPTION

Definitions

Figure 1:
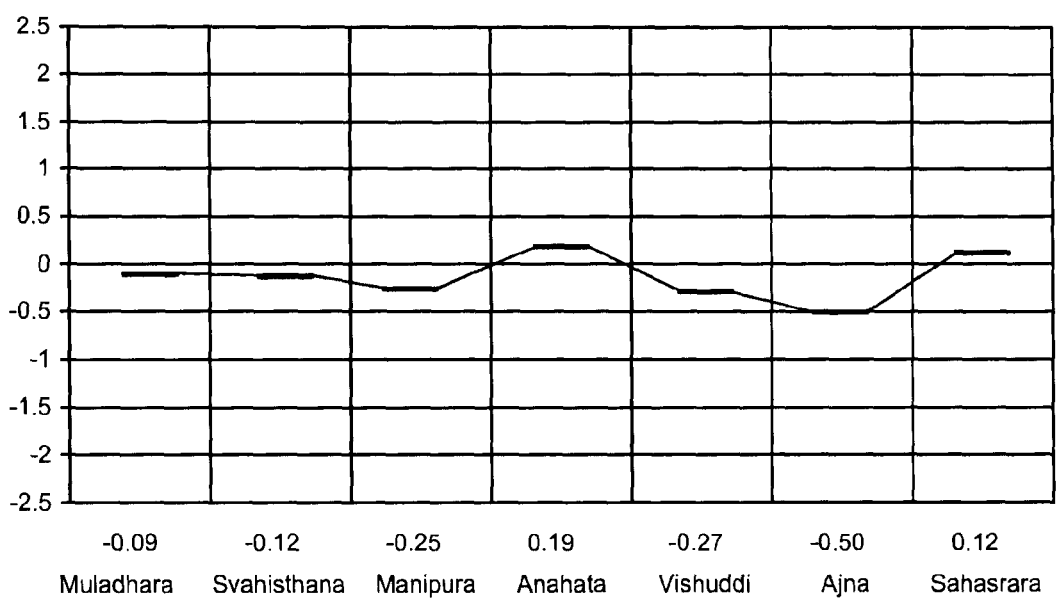
FIG. 1 depicts the biophysical construction of a healthy individual as part of the level of energy on the y axis versus each of the seven chakras on the x axis.

Chakra: The integrated energy center that is considered to affect physical, mental, emotional, and spiritual well-being of a human being. Under Eastern theories, there are seven chakras and each are positioned at various locations starting at the coccyx and rising to the crown of the head. The seven chakras are the root, spleen, solar plexus, heart, throat, brow, and crown chakras. While not wishing to be bound by any theories, it is believed that the seven chakras have a basis in anatomy such that each chakra corresponds to nerve centers and to areas of the brain, thus affording the chakras the title of "integrated energy centers." The seven chakras are traditionally referred by their number and are listed as follows:

First Chakra (Muladhara) is the integrated energy center located at the perineum, below the genitals and above the anus inside the coccyx, the pelvic plexus, base of the spine and the first three vertebrae.

Second Chakra (Svadhisthana) is the integrated energy center located in the genital region, hypogastric plexus.

Third Chakra (Manipura) is the integrated energy center located at the part of the vertebral column that corresponds to the navel region.

Fourth Chakra (Anahata) is the integrated energy center located in the heart region of the vertebral column, the cardiac plexus.

Fifth Chakra (Vishudda) is the integrated energy center located in the neck region, throat, carotoid plexus, and the cervical part of the spinal column that corresponds to the neck.

Sixth Chakra (Ajna) is the integrated energy center located at the medulla plexus, pineal plexus, and the point between the eyebrows.

Seventh Chakra (Sahasrara) is the integrated energy center located at the top of the cranium, the cerebral plexus.

GDV Technique: The Gas Discharge Visualization (GDV) technique, is based on the Kirlian Effect and employs a digitized TV matrix and image processing with specialized computer software.

Biofield: The combination of seven integrated energy centers (chakras) around the human body.

Biophysical construction: The digitized image of the biofield of the human body in response to the method of the present invention. The digitized image of the biophysical construction of the human depicts the energy level around the seven integrated energy centers of the human.

Corona Discharge: The photon emission resulting from exposing a subject to an electromagnetic field comprising of a relatively high voltage and low current.

The present invention comprises a method of evaluating the human subconscious response to smell. However, it should be noted that it is contemplated to be within the scope of the present invention that the human subconscious response to any other senses of the body may also be measured using an external stimulus.

The subconscious response may be measured by various techniques in the present invention. In one embodiment, the novel method comprises the steps of (a) evaluating a subject's biofield showing the subject's individual energy fields as a biophysical construction, (b) determining a baseline relative balance of the subject's energy fields against a defined standard for energy fields, (c) exposing the subject to at least one aroma stimulus; and (d) redetermining the comparative baseline relative balance of the subject's energy fields against the defined standard for energy fields.

The determining step (a) comprises the steps of: (a1) using a specialized camera to capture an image of the corona discharge from the fingertips of a subject and (a2) using digital software to project the images of the corona discharge from the fingertips as the biofield of the subject, and (a3) obtaining the biofield of the subject as a digitized image showing the biophysical construction of such human.

Through the GDV technique, in step (a1), an electrical component generates current through a fingerpad to a subject's fingertip. The corona discharge is captured as a glow image around the fingertip by a specialized camera, or a GDV camera. When the electrical current passes through the fingertip, the electrons are energized or "excited" to a higher state of energy by the electrical current. When the electrons cool down after moving away from the fingertip, the electrons return to their original energy level. At this point, the electrons release a photon, which is a particle form of light. The sum effect of many different electrons releasing photons from the fingertip are captured using the GDV camera, as described in step (a2) and digitized and shown as a glow around the fingertip using the specialized software. In the preferred embodiment, the corona discharge of each fingertip is read using the present inventive method.

Turning to step (a3), the digital image of the corona discharge of the fingertip is converted to show the biofield of the subject using the specialized digital software (commercially available through www.korotkov.com). Specifically, the specialized digital software uses mathematical algorithms to measure the image parameters. Quantitative values for the physical extent of the digital images, such as strength/intensity, shape, dimensions and irregularities of the cornona discharge are derived through processing the images with such specialized digital software. The algorithms correspond to different organs and systems of the body. The software utilizes a system for sector analysis of the corona discharge images whereby each individual sector or portion of the fingertip is connected energetically with specific organs and organ systems (e.g., the respiratory system). The algorithms can be found in detail in "Measuring Energy Fields, State of The Science," Dr. Konstantin Korotkov, GDV Bioelectrography Series, Vol. 1, 2004, which is hereby incorporated by reference. The specific organs or organ systems correspond to one of the seven integrated energy centers (chakras) of the body. While not wishing to be bound by any theories, it is believed that each integrated energy center resonates at a different frequency level, which can be quantitatively estimated and graphically displayed using the GDV digital software, as discussed in further detail in *Aura and Consciousness* by Dr. Konstantin Korotkov, published by St. Petersburg division of Russian Ministry of Culture, State Editing and Publishing Unit "Kultura," 1998, which is hereby incorporated by reference herein. Therefore, once the digital image of the corona discharge of the fingertip is processed through the software, the image is interpolated to show the biofield of the subject as a biophysical construction of the subject. The biophysical construction may be shown in various forms using the software. For example, the biophysical construction may be shown as an energy field around an image of a human body, or may be plotted as level of energy in relation to one or all of the integrated energy centers, or chakras.

Turning to step (b), the biophysical construction of the subject comprising the seven integrated energy centers is shown in comparison to a defined standard for energy fields. Specifically, the level of activation of each energy center is measured using GDV software as compared to a predetermined level considered to be that of a balanced subject. The predetermined level is calculated based upon statistical analysis of thousands of subjects, step (b1). See "Measuring Energy Fields, State of The Science," Dr. Konstantin Korotkov, GDV Bioelectrography Series, pp. 13-16, Vol. 1, 2004. The digital software then overlays the biophysical construction of the subject over the balance standard stored in the software to determine the baseline relative balance of the subject's integrated energy fields, step (b2). For example, FIG. 1 depicts the biophysical construction of a healthy individual as part of the level of energy on the y axis versus each of the seven chakras on the x axis. As can be seen, the level of energy for each chakra is close to 0, the standard for balance, and therefore depicts a healthy individual with relatively balanced chakras. The test subject's biophysical construction is shown in comparison to the balance standard line at 0 to show any shifts in the subject's energy fields in relation to the balance standard.

It is important to note that if one or more integrated energy centers are out of balance, then this can over time lead to physical, emotional or mental disease. Since each of the energy centers are believed to correspond to major organs and support areas in the body, keeping the seven integrated energy centers aligned can lead to a sense of health and balance which can improve the subject's life on many different levels.

See "On A Possible Psychophysiology of the Yogic Chakra System," Serena Roney-Dougal, PSI-Research-Centre, http://www.psi-researchcentre.co.uk/article_2.html.

Once the initial biophysical construction of the human is determined, the inventive method involves the step of (c) introducing an aroma stimulus such as any fragrance to the human for a predetermined period of time. The predetermined period of time is between 1 to 30 minutes, preferably between 1 to 10 minutes, and most preferably from 2 to 6 minutes. The aroma stimulus is selected from fragrances derived from plants including flowers, herbs, spices, woods, fibers and any other source known to a person of ordinary skill in the art. The oils include but are not limited to oils derived from *Abies Sibirica, Amyris Balsamifera*, Anise (*Illicium Verum*), Balm Mint (*Melissa Officinalis*), Basil (*Ocimum Basilicum*), Bay (*Pimenta Acris*), Bee Balm (*Monarda Didyma*), Bergamot (*Citrus Aurantium Bergamia*), Birch (*Betula Aba*), Bitter Orange (*Citrus Aurantium Amara*), Cabbage Rose (*Rosa Centifolia*), *Calendula Officinalis*, California Nutmeg (*Torreya Californica*), *Camellia Sinensis*, Camphor, *Capsicum Frutescers* Oleoresin, Caraway (*Carum Carvi*), Cardamon (*Elettaria Cardamomum*), Cedarwood (*Cedrus Atlantica*), *Chamaecyparis Obtusa*, Chamomile (*Anthemis Nobilis*), Cinnamon (*Cinnamomum Cassia*), Citronella (*Cymbopogon Nardus*), Clary (*Salvia Sclarea*), Clove (*Eugenia Caryophyllus*), Cloveleaf (*Eugenia Caryophyllus*), Coriander (*Coriandrum Sativum*), Coriander (*Coriandrum Sativum*) Seed, *Cyperus Esculentus*, Cypress (*Cupressus Sempervirens*), *Eucalyptus Citriodora, Eucalyptus Globulus*, Fennel (*Foeniculum Vulgare*), *Gardenia Florida, Geranium Maculatum*, Ginger (*Zingiber Officinale*), Gold of Pleasure (*Camelina Sativa*), Grapefruit (*Citrus Grandis*), Hops (*Humulus Lupulus*), *Hypericum Perforatum, Hyptis Suaveolens*, Indigo Bush (*Dalea Spinosa*), Jasmine (*Jasminum Officinale*), *Juniperus Communis, Juniperus Virginiana*, Labdanum (*Cistus Labdaniferus*), Laurel (*Laurus Nobilis*), Lavandin (*Lavandula Hybrida*), Lavender (*Lavandula Angustifolia*), Lemon (*Citrus Medica Limonum*), Lemongrass (*Cymbopogon Schoenanthus*), *Leptospermum Scoparium*, Lime (*Citrus Aurantifolia*), Linden (*Tilia Cordata*), *Litsea Cubeba*, Lovage (*Levisticum Officinale*), Mandarin Orange (*Citrus Nobilis*), Marjoram, Massoy Bark, Matricaria (*Chamomilla Recutita*), Moroccan Chamomile, Musk Rose (*Rosa Moschata*), Myrrh (*Commiphora Myrrha*), Myrtle (*Myrtus Communis*), Norway Spruce (*Picea Excelsa*), Nutmeg (*Myristica Fragrans*), *Olax Dissitiflora*, Olibanum, Opoponax, Orange (*Citrus Aurantium Dulcis*) Flower, Orange (*Citrus Aurantium Dulcis*), Palmarosa (*Cymbopogon Martini*), Parsley (*Carum Petroselinum*) Seed, Passionflower (*Passiflora Incarnata*), Patchouli (*Pogcstemon Cablin*), *Pelargonium Graveolens*, Pennyroyal (*Mentha Pulegium*), Peppermint (*Mentha Piperita*), Pettigrain, Pine (*Pinus Palustris*), Pine (*Pinus Palustris*) Tar, Pine (*Pinus Pinea*) Kernel, Pine (*Pinus Pumiho*), Pine (*Pinus Sylvestris*) Cone, Rosemary (*Rosmarinus Officinalis*), Rose, Rosewood (*Aniba Rosseodora*), Rue (*Ruts Graveolens*), Sage (*Salvia Officinalis*), *Sambucus Nigra*, Sandalwood (*Santalum Album*), Sandarac (*Callitris Quadrivalvis*) Gum, *Sassafras Officinale, Sisymbrium Ino*, Spearmint (*Mentha Viridis*), Sweet Marjoram (*Origanum Majorana*), Sweet Violet (*Viola Odorata*), Tar, *Thuja Occidentalis*, Thyme (*Thymus Vulgaris*), *Vetiveria Zizanoides*, Wild Mint (*Mentha Arvensis*), *Ximenia Americana*, Yarrow (*Achillea Millefolium*), Ylang Yang (*Cananga Odorata*), or any combinations thereof.

Powder forms of gemstones may also be incorporated into formulations of the present invention because of their intrinsic energy level. Intrinsic energy level of an ingredient is measured as a change in the coronoa discharge of an individual as indicated by the GDV technique of the present inventive method. Gemstones of the present invention include but are not limited to malachite, lapis, tourmaline, citrine, amethyst, tiger's eye, aquamarine, and lazurite.

Figure 2:
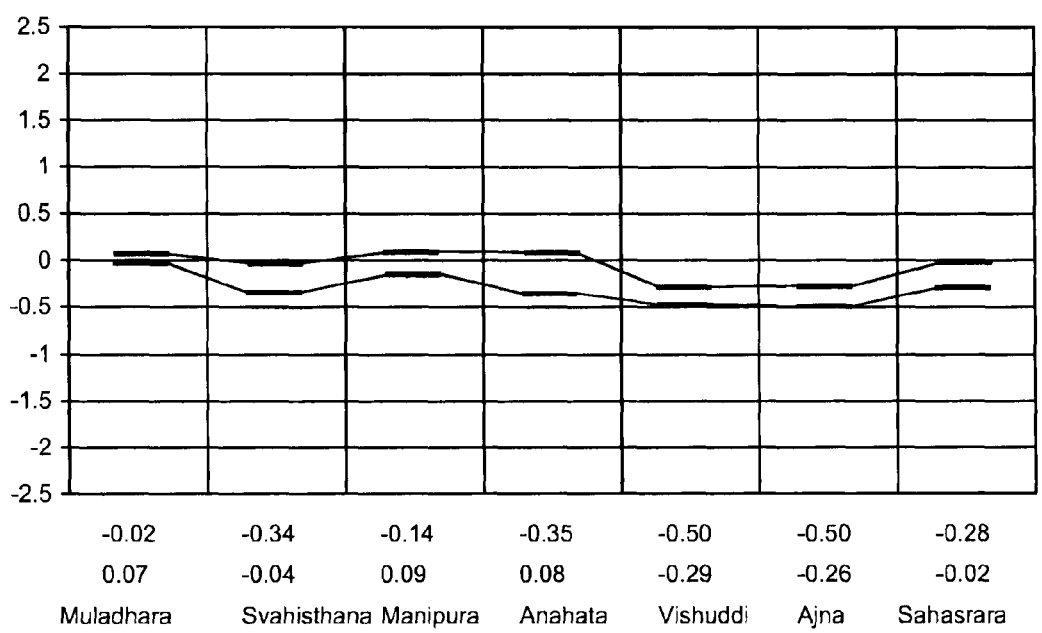
FIG. 2 depicts the measurement of the energy level of a test subject's corona discharge in relation to the form coefficient, which is a measure of the shape of the corona discharge.
Figure 3:
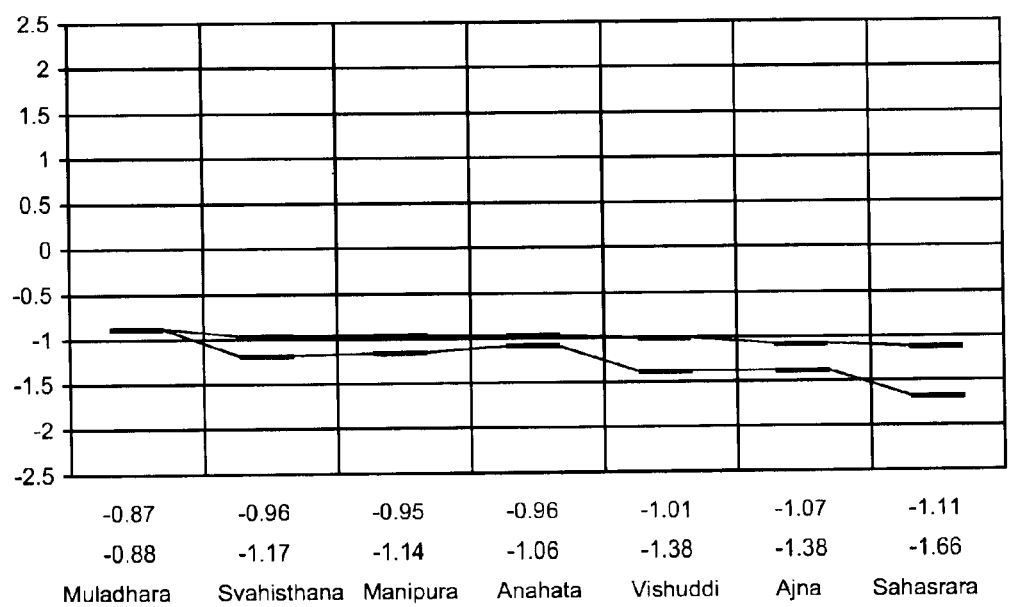
FIG. 3 depicts the change in a test subject's biophysical construction before and after exposure to a peppermint oil aroma.
Figure 4:
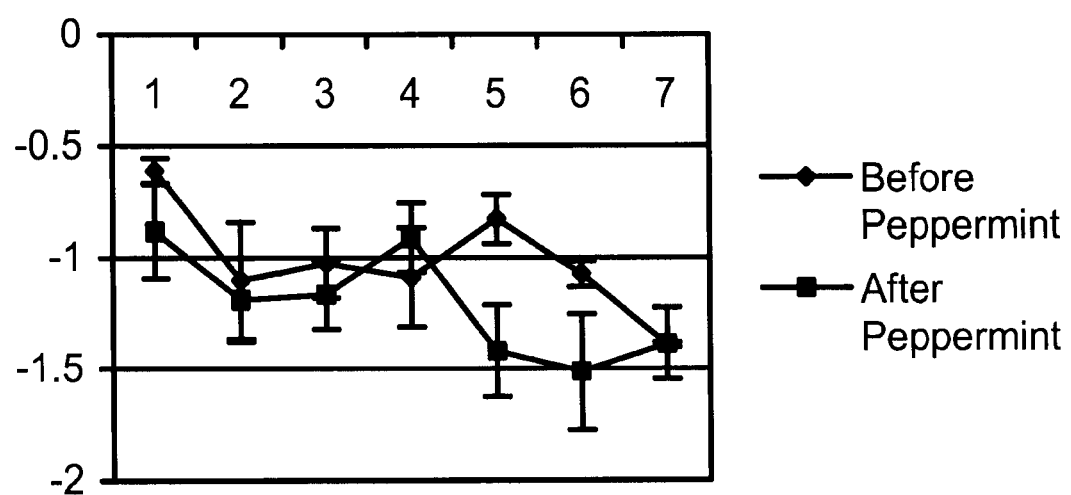
FIGS. 4-11 depict representations of the effect of various aroma stimuli on a test subject.
Figure 5:
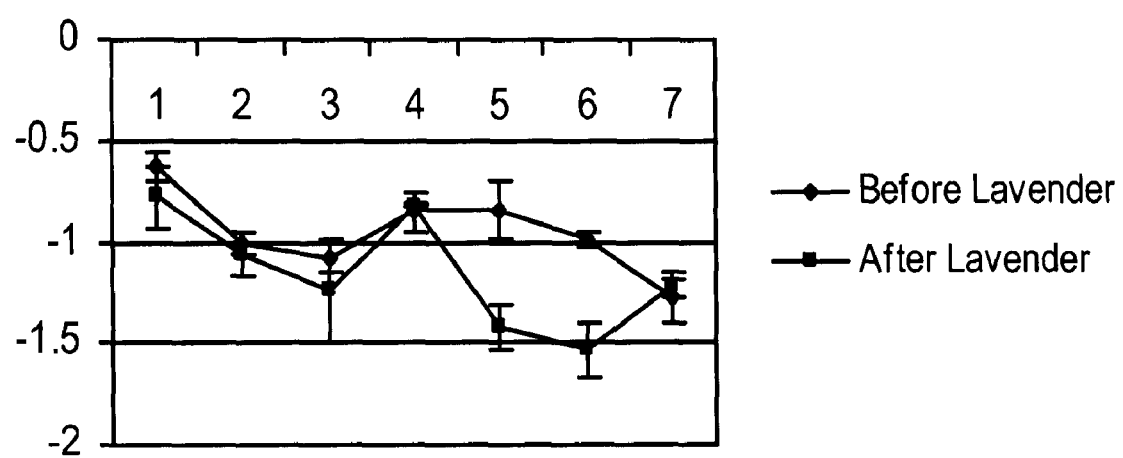
Figure 6:
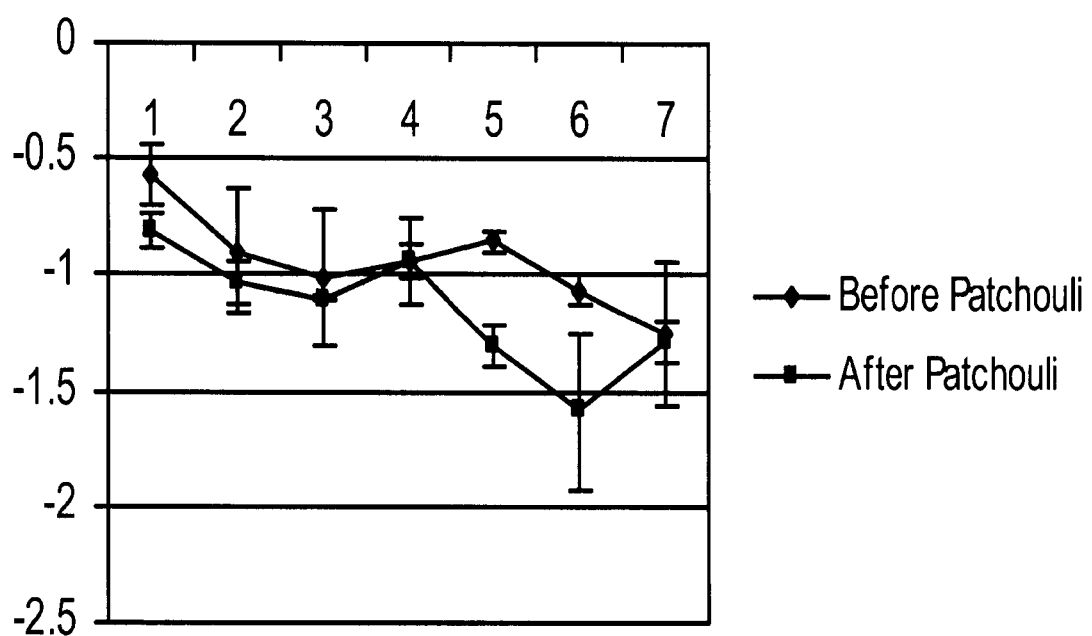
Figure 7:
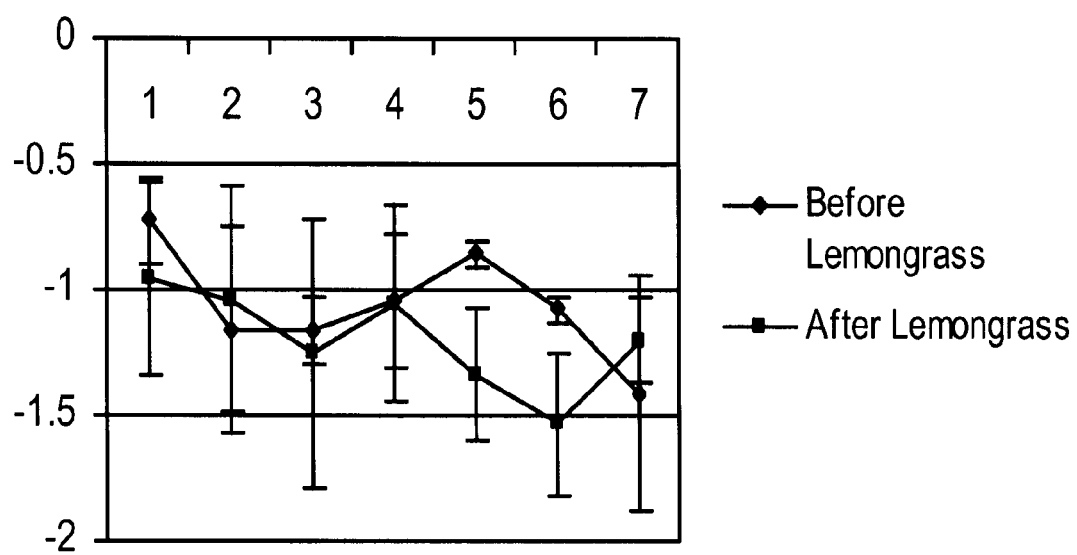
Figure 8:
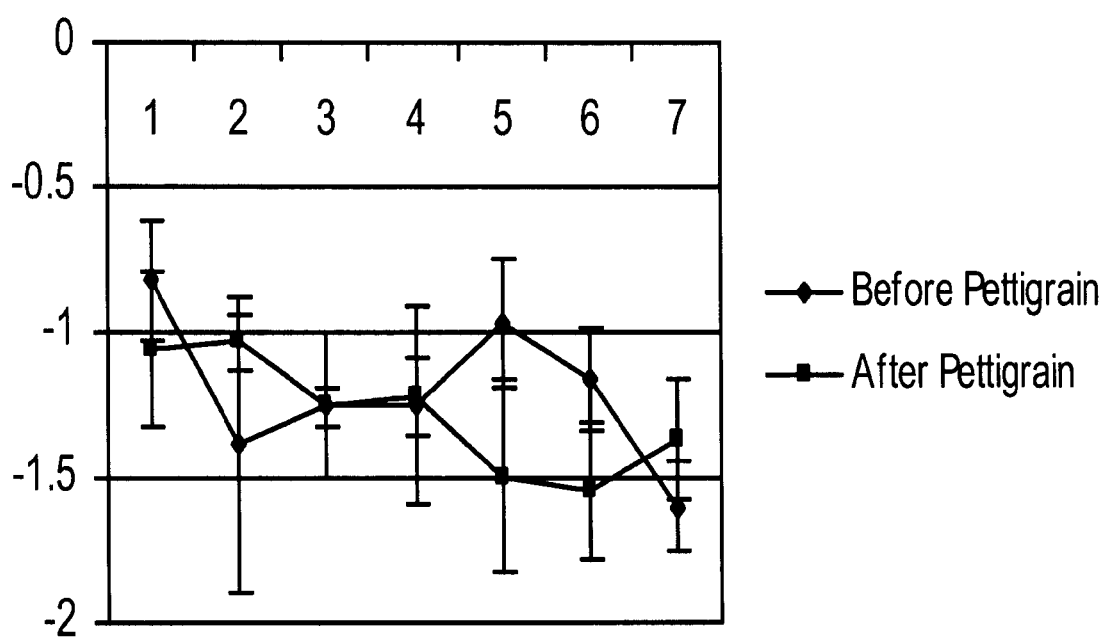
Figure 9:
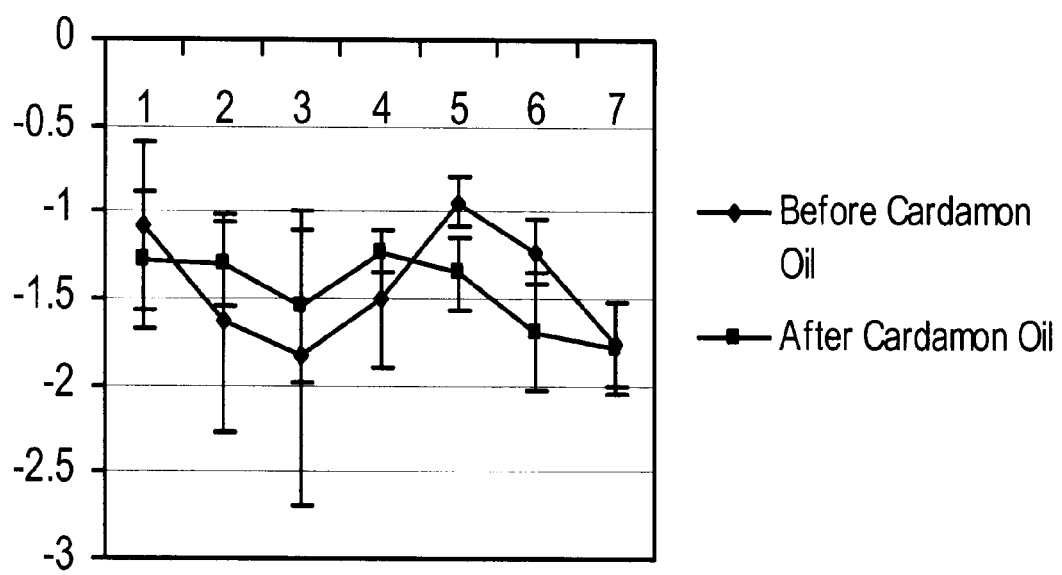
Figure 10:
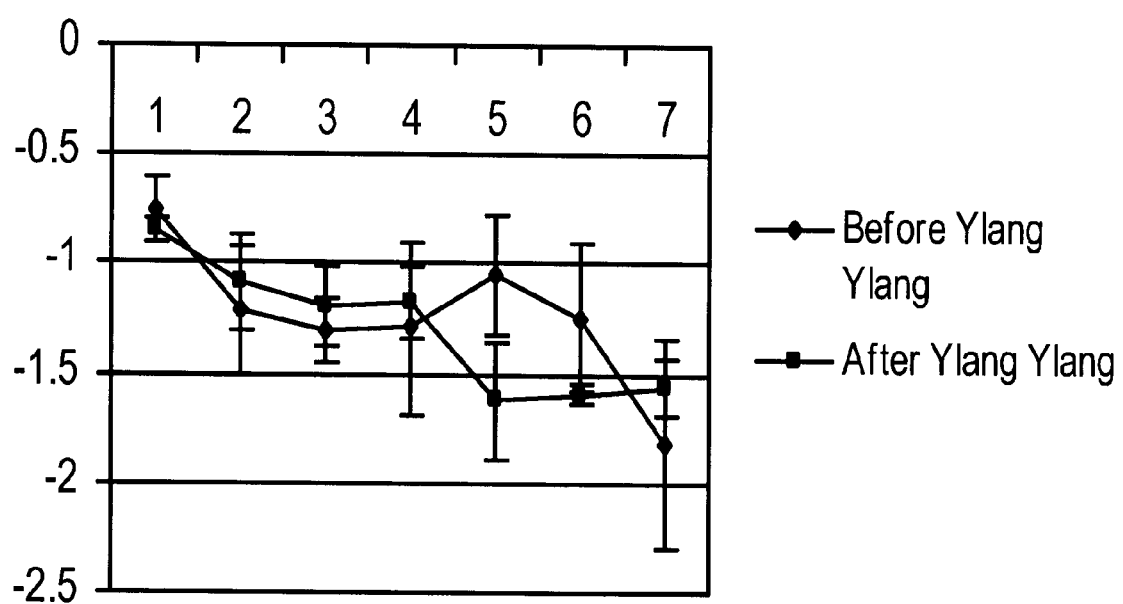
Figure 11:
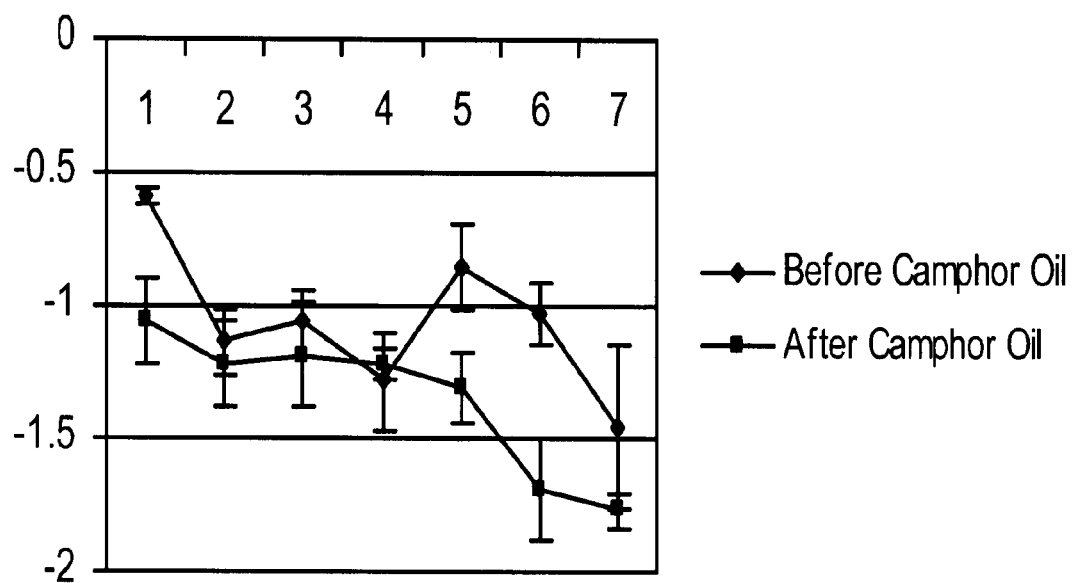

The redetermining step (d) comprises repeating steps (a1), (a2) and (a3) after the human has been exposed to the fragrance for the predetermined period of time. In the redetermining step, the subconscious response to the aroma stimulus is shown using the noninvasive GDV technique. Such a subconscious response measures, for example, the subject's adaptation stage to the aroma stimulus and/or the subject's subconscious response to the intrinsic energy emitted by the aroma stimulus. The adaptation stage is measured as the time involved for the subject's subconscious to adjust to the stimulus to the body's senses through smell, as shown in FIG. 2. Specifically, FIG. 2 depicts the measurement of the energy level of a test subject's corona discharge in relation to the form coefficient, which is a measure of the shape of the corona discharge. The adaptation stage is depicted in Stage B in FIG. 2. The biophysical construction of the subject in response to the aroma stimulus can then be compared to the biophysical construction of the subject prior to exposure to such stimulus, using the digital software, as shown for example in FIG. 3. FIG. 3 depicts the change in a test subject's biophysical construction before and after exposure to a peppermint oil aroma. FIGS. 4-11 are further representative of the effect of various aroma stimuli on a test subject. The effect is shown as the energy level corresponding to each of the integrated energy centers before and after the test subject was exposed to each aroma.

In an alternate embodiment, the inventive method further comprises the step (e) comprises the steps of repeating steps (a) through (d) above until the desired balance against the defined standard of energy fields is achieved. In utilizing step (e), the present method enables a means of determining imbalance in different integrated energy centers and minimizes such imbalance through the use of aroma stimulus, as shown in Example 2 below and FIGS. 14-15. Specifically, once the changes have been analyzed, diagnosis may be made as to human responses to different aromas to prescribe fragrances which would effectively help the human subject for various conditions such as stress, anxiety, fear, weakness and depression, as discussed in further detail in *Color and Crystals: A Journey Through the Chakras* by Joy Gardner-Gordon, Crossings Press; Freedom, Calif. 95019, 1988 and wwv.healing.about.com Moreover, human responses to different intrinsic energy can aid in formulating cosmetic compositions which incorporate ingredients with the most suitable intrinsic energy.

In another alternate embodiment, the human subconscious response to a smell, or an aroma stimulus, can be measured using quantitative analysis of the corona discharge of a subject's fingertip. Specifically, the inventive method of evaluating a subject's subconscious response to an aroma stimulus comprises the steps of (a) reading a subject's corona discharge at predetermined intervals for a predetermined period of time; (b) determining a baseline measurement of the subject's corona discharge prior to exposure to an aroma stimulus; (c) exposing the subject to at least one aroma stimulus; (d) reading the subject's corona discharge throughout exposure to the aroma stimulus at the predetermined intervals; (e) redetermining a measurement of the subject's corona discharge for the predetermined period of time; and (f) reading the subject's corona discharge after exposure to the aroma stimulus at the predetermined intervals for the predetermined period of time to determine the final measurement of the subject's corona discharge.

Turning to step (a), the subject's fingertip is first exposed to an electrical current generated by the GDV technique as described hereinabove to read the corona discharge from such exposure in step (a1). The digital software then projects the reading into a digital image of the corona discharge in step (a2). In the present method, one fingertip or all fingertips may be read using the GDV system. Preferably, only the left ring finger is used for the reading based on numerous experiments which indicated that reading only the left ring fingertip provides results that are statistically equivalent to the results of a reading of all ten fingertips.

Turning to step (b), the digitized image is processed through the digital software to determine a balance standard for corona discharge of that subject's subconscious state using statistical analysis in step (b1). In step (b2), the images of the corona discharge are then interpreted as quantitative data points using the digital software, so that the quantitative data points can be shown graphically for ready analysis. The quantitative data points representing each reading of the corona discharge of the subject's fingerprint are interpreted in terms of parameters selected from the group consisting of area of the image of the corona discharge, intensity of the image of corona discharge and shape of the image of the corona discharge. For example, in FIG. 2, the corona discharge is measured in terms of a form coefficient, or shape of the corona discharge. In the present method, either one or several readings can be taken of each fingertip. In the preferred method, at least three readings are taken to obtain one averaged quantitative data point to represent the corona discharge at each stage of the readings. The balance standard is taken for a predetermined period of time of between 1 minute to 10 days, preferably from minutes to 5 days, and most preferably from 5 minutes to 15 minutes.

Turning to step (c), the subject is then exposed to at least one aroma stimulus for a predetermined period of time. The predetermined period of time is between 1 to 30 minutes, preferably from 1 to 20 minutes, and most preferably from 2 to 6 minutes. The aroma stimulus may be chosen from any of the materials disclosed hereinabove, but are not limited thereto.

Figure 12:
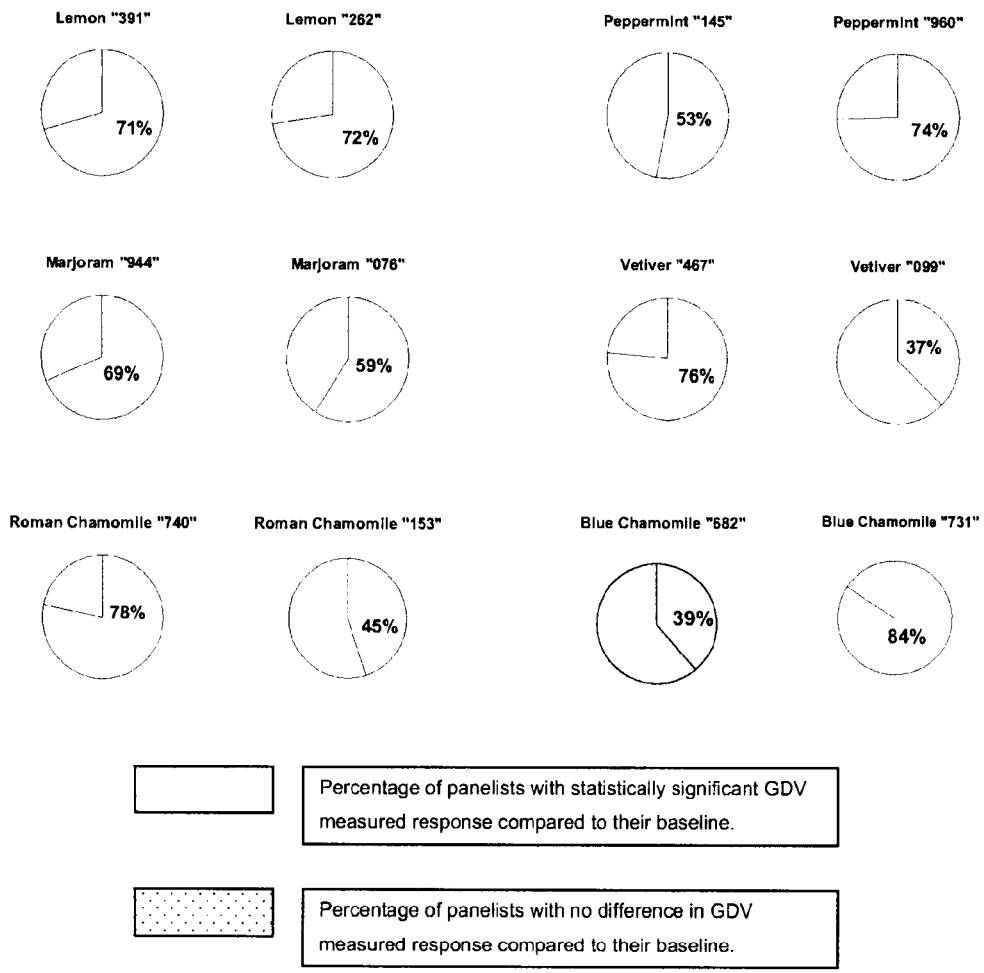
FIG. 12 provides a summary of the responses of several test subjects to exposure to selected oils.

The subject's corona discharge is re-read at predetermined intervals of between 1 to 30 seconds, preferably from 2 to 20 seconds, and most preferably every 15 seconds throughout the duration of subject's exposure to the aroma stimulus in step (d). The digital software redetermines a measurement of the subject's corona discharge for the predetermined period of time during exposure to the aroma stimulus in step (e). Finally, in step (f), the subject's corona discharge after exposure to the aroma stimulus at the predetermined intervals for the predetermined period of time is read to determine the final measurement of the subject's corona discharge. FIG. 12 provides a summary of the responses of several test subjects to exposure to selected oils. As can be seen in the Figure, some test subjects had no statistically significant response to certain aromas.

The present inventive methods therefore allow analysis of the subject's subconscious response to an aroma stimulus by comparing the measurements of the subconscious response prior to exposure to an aroma stimulus, during exposure to the aroma stimulus and after exposure to the aroma stimulus, in optional step (g), as shown in representative FIG. 3 in direct relation to corona discharge and FIGS. 4-11 in relation to chakras. Once the changes have been analyzed, diagnosis may be made as to human responses to different aromas to prescribe fragrances which would effectively help the human subject for various conditions such as, for example, stress, anxiety, fear, weakness and depression as well as aiding in creating energizing, balancing and calming effects, as discussed in Example 1 below. Moreover, human responses to different intrinsic energy of materials can aid in formulating cosmetic compositions which incorporate ingredients with the most suitable intrinsic energy for that subject, as shown in Example 1 below. For example, certain organic oils may have a different intrinsic energy than that oil in a non-organic form. Although this difference may not be sensed consciously, the present inventive method is used to evaluate the subconscious response to an oil in both organic and non-organic form, as seen in Example 2 below.

The present invention is further illustrated by the following non-limiting examples.

Example 1

The following example shows the use of the inventive method to test the intrinsic energy of certain gemstones incorporated into oils and to further clinically test those gemstone containing oils on test subjects to evaluate subconscious response.

1. Testing Oils Containing Gemstones

Three chakra blends with various concentrations of powdered gemstones are tested by using a glass slide with a cylindrical hole milled therein, which centers and controls size of sample drops. Sample drops of each chakra blend are dropped on the glass slide and tested using the GDV technique to test the energy levels for each blend. The chakra blends tested are blends of oils believed to correspond to effecting chakra 1, chakra 4 and chakra 7, respectively. The Chakra 1 formulation is tested with concentrations of powdered quartz and rhodocrosite incorporated therein, the Chakra 4 formulation is tested with concentrations of powdered malachite and tourmaline incorporated therein, and the Chakra 7 formulation is tested with concentrations of powdered calcite and quartz incorporated therein. The results are shown in Tables 1, 2 and 3, respectively.

TABLE 1

The Chakra 1 and Quartz and Rhodocrosite Scenario

| TESTED SAMPLE | ASCENDING RANK IN TERMS OF AVERAGE INTENSITY (1 = LOWEST) |
|---|---|
| 1 NS | 1 = LOWEST |
| 1 Q 0.001% NS | 2 |
| 1 Q 0.01% NS | TIED FOR 4 = HIGHEST |
| 1 Q 0.1% NS | TIED FOR 3 |
| 1 R 0.001% NS | TIED FOR 3 |
| 1 R 0.01% NS | TIED FOR 3 |
| 1 R 0.1% NS | TIED FOR 4 = HIGHEST |

1 = CHAKRA ONE;
Q = QUARTZ;
R = RHODOCROSITE;
NS = NO SOLUBILIZER

TABLE 2

The Chakra 4 and Malachite and Tourmaline Scenario

| TESTED SAMPLE | ASCENDING RANK IN TERMS OF AVERAGE INTENSITY (1 = LOWEST) |
|---|---|
| 4 NS | 1 = LOWEST |
| 4 M 0.001% NS | 2 |

TABLE 2-continued

The Chakra 4 and Malachite and Tourmaline Scenario

| TESTED SAMPLE | ASCENDING RANK IN TERMS OF AVERAGE INTENSITY (1 = LOWEST) |
|---|---|
| 4 M 0.01% NS | 3 |
| 4 M 0.1% NS | 4 |
| 4 T 0.001% NS | TIED FOR 5 = HIGHEST |
| 4 T 0.01% NS | TIED FOR 5 = HIGHEST |
| 4 T 0.1% NS | TIED FOR 5 = HIGHEST |

4 = CHAKRA FOUR;
M = MALACHITE;
T = TOURMALINE;
NS = NO SOLUBILIZER

TABLE 3

The Chakra 7 and Calcite and Quartz Scenario

| TESTED SAMPLE | ASCENDING RANK IN TERMS OF AVERAGE INTENSITY (1 = LOWEST) |
|---|---|
| 7 NS | 1 = LOWEST |
| 7 C 0.001% NS | 2 |
| 7 C 0.01% NS | 3 |
| 7 C 0.1% NS | 4 |
| 7 Q 0.001% NS | TIED FOR 5 = HIGHEST |
| 7 Q 0.01% NS | TIED FOR 5 = HIGHEST |
| 7 Q 0.1% NS | TIED FOR 5 = HIGHEST |

7 = CHAKRA SEVEN;
C = CALCITE;
Q = QUARTZ;
NS = NO SOLUBILIZER

The results from Tables 1-3 above show that the blends containing gemstones show a higher GDV activity level than the pure blends. Further, the Tables show that different levels of concentration of the gemstone powders show different levels of measured GDV activity.

While some samples showed a higher level of activity at 0.1%, this activity is not times as high as that of the 0.01% solution. There are diminishing returns when increasing the concentration of powdered gemstones in the chakra blend formulations. Therefore, it is determined that a concentration of 0.05% is the most efficient in terms of activity per unit of volume, and aesthetics for the finished product. This concentration is therefore recommended for formulation of Chakra blend formulations containing blends of oils and powdered gemstones believed to correspond to each of the seven chakras.

2. Clinical Trials of Reformulated Blends

After successful direct testing of the blends with the GDV technique of the present invention, the human subconscious reaction to the aromas of these oils is tested.

The blends are tested to determine the effect they have on the holistic state of the body.

This testing is done with the GDV technique of the present invention utilizing chakra analysis.

Protocol

1. Test subject arrives at testing center.
2. The "baseline" of test subject (before exposure to chakra blend) is established by:
   a. Measurement of test subject's biofield incorporating each of the seven individual chakras using static GDV.
   b. Completion of mood mapping questionnaire (for individual chakra), in order to assess mood.
3. Test subject is exposed to Chakra blend by smelling blends for 2 minutes.
4. The individual's chakras are measured with static GDV, following exposure to oil blend.
5. After a five-minute wait, panelist's chakras are tested again.

The individual's mood mapping is re-tested (for individual Chakra) following exposure to oil blend.

Chakra Analysis

The present inventive method utilizes Chakra analysis in the GDV digital software to analyze GDV images of the fingertips to derive data on relative "energy levels" of the body's chakras. It charts a value for each Chakra on a scale of −2.5 to +2.5. Values can be compared to indicate relative changes over time. For instance, a baseline reading can be taken, followed by an olfactory or skin test, and then a second reading taken to determine any effect. This is the approach used in this study.

Figure 13:
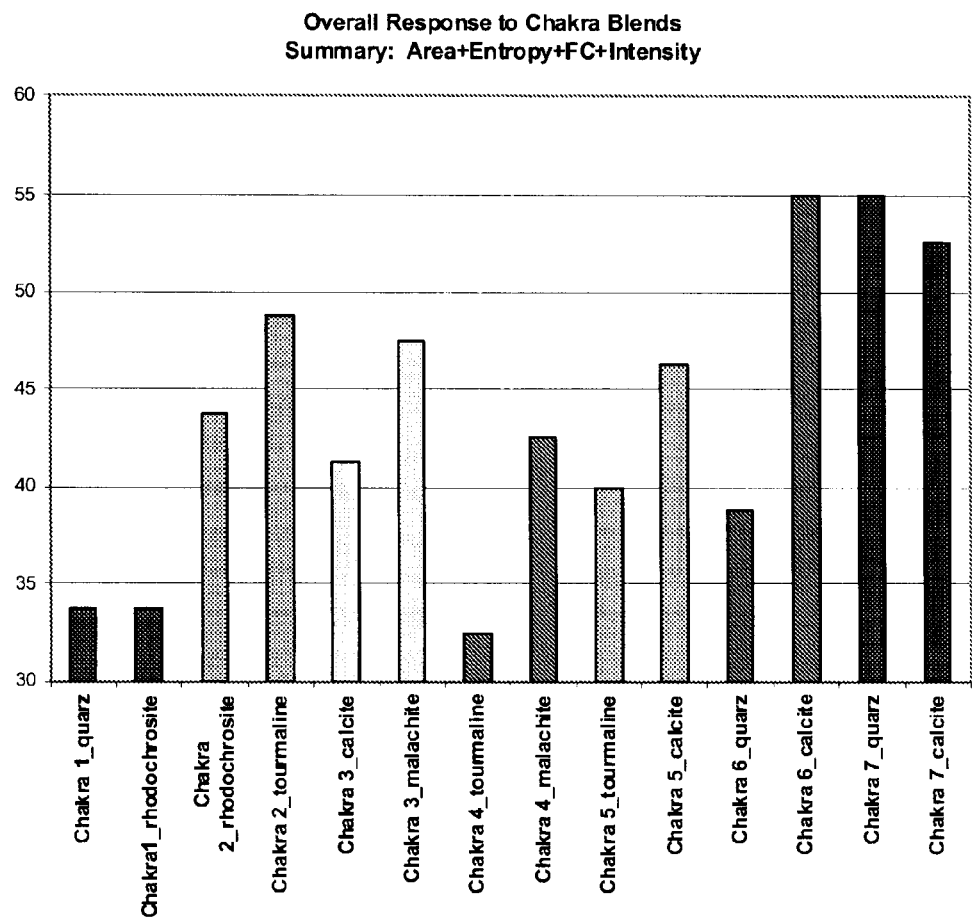
FIG. 13 depicts the overall GDV response to gemstone blends.

Two samples of each Chakra oil blend corresponding to each of the seven chakras incorporating different powdered gemstone are prepared. These are tested to determine which gemstone elicits a more desirable effect in the panelists. The holistic effect of these blends upon the body is determined by two techniques—the GDV Chakra analysis and the GDV measurement of physical response to olfactory stimulation, or through direct analysis of the corona discharge. The latter technique combines parameters of Intensity, Area, Form Coefficient and Entropy to indicate the level of response to an aroma stimulus. FIG. 13 shows the differing responses to the two samples for each Chakra blend.

As can be seen in FIG. 13, each Chakra formulation is tested twice, with two different powdered gemstones incorporated therein for each test. As can be seen, in most cases, overall holistic response to one of the gemstone blends is higher than the other for each chakra formulation, with the exception of Chakra 1. A higher value in the GDV response indicates a favorable GDV response to such a formulation for the Chakra tested. In Chakra 1, because quartz is the obvious choice for Chakra 7 with a response of 55, rhodocrosite is recommended over quartz for Chakra 1. The recommended Chakra blend for Chakra 1 incorporates Rhodacrosite or Quartz, Chakra 2 blend incorporates Tourmaline (over Rhodacrosite), Chakra 3 blend incorporates Malachite (over Calcite), Chakra 4 blend incorporates Malachite (over Tourmaline), Chakra 5 blend incorporates Calcite (over Tourmaline), Chakra 6 blend incorporates Calcite (over Quartz), and Chakra 7 incorporates Quartz (over Calcite).

Figure 14:
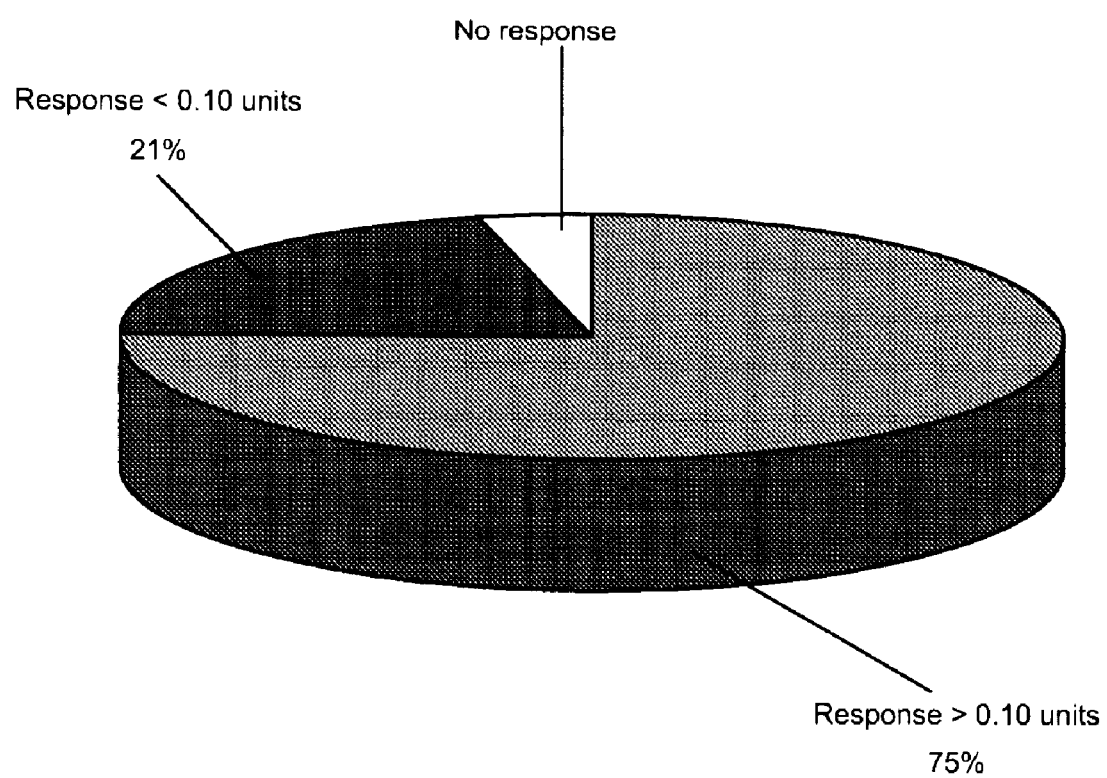
FIG. 14 provides the Cumulative Distribution of Panelist Response After Exposure to Test Chakra/Gemstone Formulations, as tested in Example 1 of the present invention.
Figure 15:
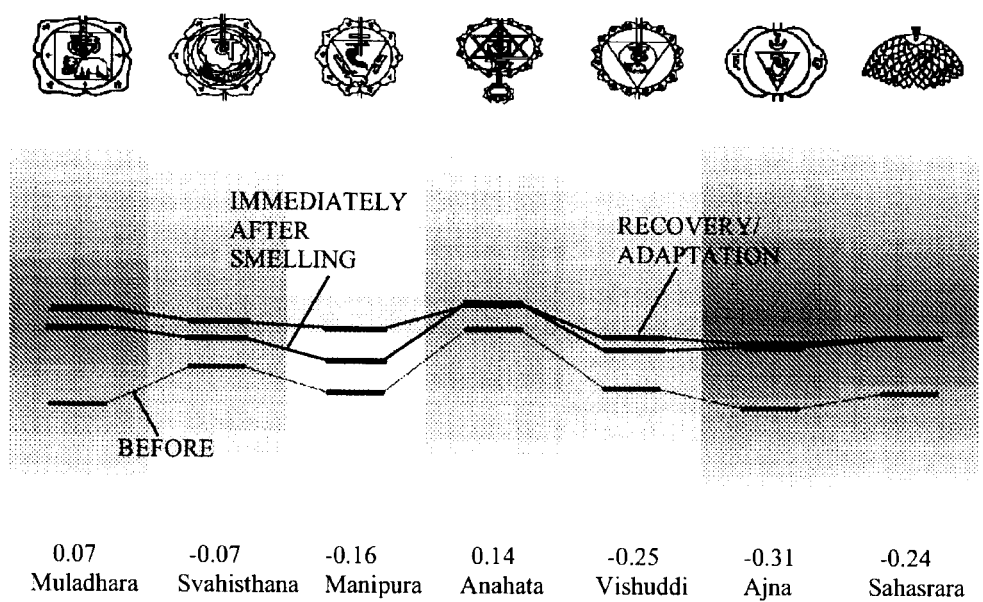
FIG. 15 provides the results of the effect of certain aroma stimuli on balancing the energy levels corresponding to the seven Chakras in Example 1 of the present invention.

The results of the clinical study are shown in FIG. 14 and show that a high percentage of the panelists in this study show a difference in GDV Chakra activity after exposure to the oils. At least ninety five percent (95%) of data points fall within the range of −0.2 to −1.0. If a threshold of 0.1 units is set as representing a response, then seventy five percent (75%) of panelists respond to the Chakra blend. An additional twenty one percent (21%) of panelists show a response less than 0.1 units. Therefore, ninety six percent (96%) of panelists respond to the Chakra blends.

In other words, the GDV Chakra analysis of the present inventive method is sensitive to the holistic subconscious human reaction to essential oil blends containing gemstones. However, it is contemplated that essential oil blends alone, without incorporation gemstones believed to affect subconscious reponse due to their intrinsic energy, also produce a holistic subconscious human reaction that is measurable by the GDV chakra analysis of the present invention.

Charting Chakra-Specific Response

When comparing results from the last Chakra measurement to the baseline measurements, several statistical effects can be seen. They can be summed up as "energizing," "calming," and "balancing." The "balancing" effect is illustrated well with this experiment, and comes closest to the desired effect of the product. The other types of analysis may be useful in the future for other products.

Energizing

This is seen as a rise in value for the Chakra data. For example, a change from −1.4 to −0.6 or a change from 1.0 to 1.6 would be in this category. Averaging readings obscures whether they are moving from a subzero or positive baseline.

Calming

This is seen as a decrease in value for the Chakra data. For example, a change from 1.8 to 0.2 or a change from −1.0 to −1.7 would be in this category. As in the energizing case, averaging together these measurements obscures whether they are moving from a subzero or positive baseline.

Balancing

This analysis looks at the panelists that exhibit Chakra values that are moving toward zero over the course of the test. This movement indicates a balancing or normalization of the Chakra activity. Looking at the data in this way better mirrors the desired effect of products incorporating ingredients geared towards affecting each of the seven chakras.

In the present study, the number of people exhibiting a balancing trend is used to observe whether the product is doing what it is designed to do. Specifically, this study tests whether a specific Chakra blend formulation has an effect on its respective Chakra. The results are provided in FIG. 15, which shows that after smelling an aroma stimulus, the energy levels corresponding to the Chakras are more balanced, or tend to come closer to the standard for balance, the zero line.

Figure 16:
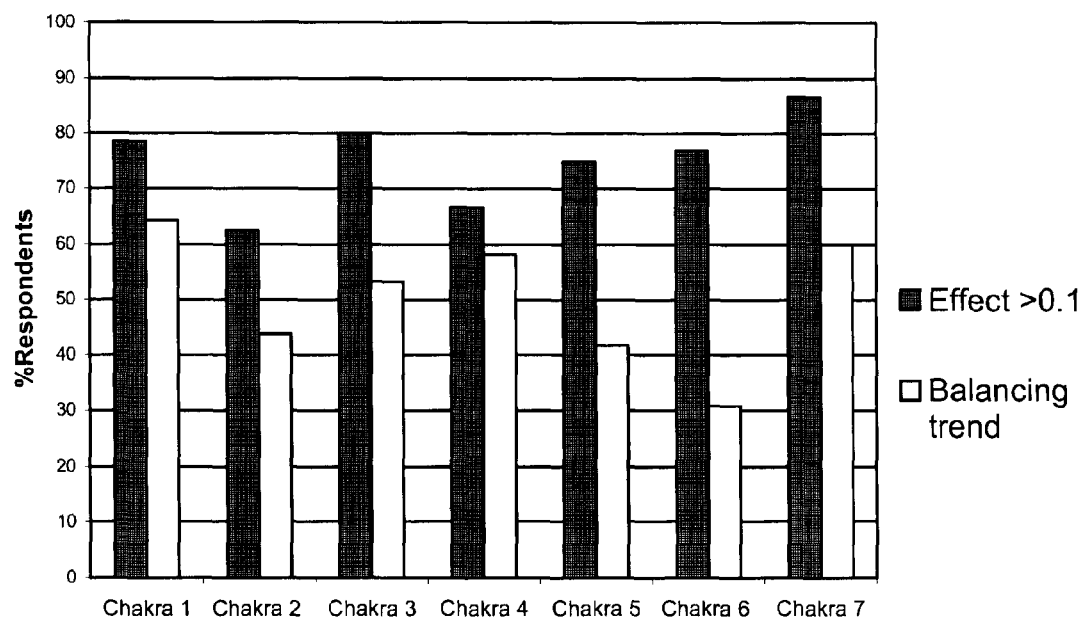
FIG. 16 provides the results of the effect that each oil blend has on its respective Chakra in Example 1 of the present invention.

FIG. 16 provides the results of the effect that each oil blend has on its respective Chakra. Two trends are observed in GDV Chakra analysis of the present invention, two trends:

1. An individual Chakra is affected by its blend, expressed as a percentage of panelists showing a response of at least 0.1 units difference between their baseline reading and the one taken after smelling the blend (measure of statistical significance).
2. The number of panelists who show a movement toward zero (the most desirable state).

In the first case, it is seen that there is a response rate of at least 75% for the Chakra blends on their respective Chakra in cases 1, 3, 5, 6, and 7. In the second case, the balancing effect is seen in a smaller percentage of the panelists. This is to be expected, as the balancing effect is more specific and is a more individual response. In other words, it is easier to register any change across a large sample population than it is to register a true balancing effect.

Conclusions

The present inventive method may be used to
a) Identify appropriate gemstones for each Chakra, and their optimum use level in the essential oil formulations.
b) Demonstrate holistic effects of Chakra blends containing gemstones on the human body; and
c) Observe noticeable human response to Chakra blends containing gemstones in a majority of cases (75%).

Further, the present inventive method utilizing the Chakra analysis can be used to register individual Chakra response to test formulations. For this type of analysis, more detailed studies focusing on individual panelists may be conducted, as physiological response is unique to the individual.

Example 2

The following example shows the use of the inventive method to note differences in the intrinsic energy of various oils having aroma stimuli.

Twelve samples, representing a conventionally produced and an organically produced sample of 6 different essential oils (Lemon, Peppermint, Marjoram, Roman Chamomile, Vetiver, Blue Chamomile) are provided under double-blind conditions to the test subjects. The samples are identified to the test subjects only by number. These oils are selected from a group of several dozen essential oils. Gas chromatography analysis is used to compare conventionally-processed and organically-processed samples of each oil in this group. The six oils in this test show virtually no difference in this analysis between the two samples, meaning they are extremely similar chemically.

The panelists came from a group of volunteers, consisting of 17 young women and 11 middle-aged men. All panelists are practically healthy, and free of common allergies.

GDV measurements are taken after the panelists had remained in a relaxed environment for at least twenty minutes. Testing is done in a darkened room to minimize any visual cues or distractions. Ventilation is controlled to ensure consistent conditions.

The measurement protocol for each panelist included several stages:

A. 5-minute baseline period. GDV readings of the left ring finger taken every 15 seconds.
B. Smelling of the sample for 2.5 minutes, with GDV readings of the left ring finger taken every 15 seconds.
C. 5-minute aftereffect testing, in absence of aroma; GDV readings taken every 15 seconds.

Thus, there are 50 experimental points for each session and approximately 1400 for each sample. Next, steps A-C are repeated for the second oil sample, and again for the third sample. The decision to center testing on the left ring finger is based on research that shows that this particular finger is most suited for GDV analysis of overall physiological states. "Measuring Energy Fields, State of The Science," Dr. Konstantin Korotkov, GDV Bioelectrography Series, Vol. 1, 2004. Smelling of coffee operates as a control to "clear" the olfactory signals from the preceding test. The effectiveness of this technique is confirmed by comparing subsequent GDV readings with earlier results. In one day a particular panelist is exposed to not more than three different oils. Results for one representative panelist are shown in FIG. 2.

A preferences test is then administered to the panelists. This is done to quantify the conscious reaction to the aroma and in order to better analyze the GDV results. Panelists rank the oils on two scales:

1. A subjective rating, in which panelists could pick any whole number between 1 and 6 inclusive to describe the pleasantness of the aroma. 1 represented a strong dislike, and 6 a strong preference. This value was represented as "a."
2. The panelists are also asked to force-rank the oils from 1 to 6, with 1 representing the best-smelling oil and 6 the worst smelling. Each number would represent only one oil, and every oil has to be ranked. This value is represented as "b."

A formula is created to combine these results into an overall preference rating, "C." The number of oils, in this test always 6, is represented as N in the following formula: C=a (1−b/(N+1)).

TABLE 4

PREFERENCE RATING

| Oil | Free rating (a) | Forced Rank (b) | Average (c) |
|---|---|---|---|
| Lemon | 4.56 | 1.19 | 3.81 |
| Peppermint | 3.81 | 2.31 | 2.62 |
| Marjoram | 2.94 | 3.50 | 1.51 |
| Roman Chamomile | 2.69 | 3.94 | 1.25 |
| Vetiver | 2.13 | 4.69 | 0.84 |
| Blue Chamomile | 1.94 | 5.38 | 0.58 |

As seen in Table 4, the participants greatly prefer lemon and peppermint over other scents and show the conscious reaction to aroma stimuli.

The present inventive method is then employed to test the subconscious response to aroma stimuli to compare to the conscious response. Five different GDV parameters are measured. Of these five, three show significant and consistent variation: area (apparent size of the corona discharge, measured in pixels), form coefficient (measure of the similarity of the discharge's shape to a circle: 1 indicates a perfect circle, higher numbers indicate increasingly uneven borders), and intensity (brightness of the phenomenon, units based on visual brightness measured on a scale of 1-255).

The results of each of the readings are charted to show change in each parameter for each panelist over time, as seen in FIG. 2. The results of the readings for each of the parameters for each oil tested are shown in Table 5 below.

TABLE 5

PERCENTAGE OF PANELISTS WITH SIGNIFICANT GDV-MEASURED REACTION TO AROMA STIMULI

| Oil | Lemon | | Marjoram | | Peppermint | | Roman Chamomile | | Blue Chamomile | | Vetiver | |
|---|---|---|---|---|---|---|---|---|---|---|---|---|
| Sample # | 391 | 262 | 076 | 944 | 145 | 960 | 153 | 740 | 682 | 731 | 099 | 467 |
| GDV Area | 76.5 | 58.8 | 76.0 | 76.4 | 65.0 | 82.4 | 71.0 | 70.6 | 47.0 | 100.0 | 41.2 | 82.4 |
| GDV FC | 88.2 | 76.5 | 65.0 | 70.5 | 59.0 | 76.5 | 24.0 | 88.2 | 12.0 | 82.3 | 47.1 | 82.4 |
| GDV Intensity | 47.1 | 82.4 | 35.0 | 58.8 | 35.0 | 64.7 | 41.0 | 76.5 | 59.0 | 70.5 | 23.5 | 64.7 |
| Average % | 70.6 | 72.5 | 59.0 | 68.6 | 53.0 | 74.5 | 45.0 | 78.4 | 39.0 | 84.3 | 37.3 | 76.5 |

As noted above, each sample for each essential oil causes a large difference in the GDV reading, depending on whether the sample is conventionally or organically produced. Therefore, a subconscious response to an aroma stimulus based on its source can be identified using the present inventive method, which is not identifiable through a conscious response.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method of comparing measurements of corona discharge of a subject prior to, during and after exposure to an external stimulus in order to evaluate the subject's subconscious response to sensory stimulation measured using the external stimulus, comprising the steps of:
    (a) evaluating the subject's corona discharge by measuring the corona discharge using a specialized camera to capture at least one image of the corona discharge from at least one fingertip of the subject prior to the exposure to the external stimulus, using digital software to project the at least one image from the at least one fingertip as at least one digitized image, and interpreting the at least one image of the corona discharge as at least one quantitative data point;
    (b) exposing the subject to the external stimulus for a predetermined period of time, during which the subject's corona discharge is measured at predetermined intervals using the specialized camera and the digital software;
    (c) measuring the subject's corona discharge using the specialized camera and the digital software after the exposure to the external stimulus; and
    (d) comparing the measurements obtained before, during and after exposure to the external stimulus to evaluate the subject's overall subconscious response to the external stimulus.

2. The method of claim 1 wherein step (a) further comprises the steps of:
    determining a baseline measurement of the subjects energy fields based on the corona discharge prior to exposure to the external stimulus; determining a balance standard for energy fields using statistical analysis measured from thousands of subjects wherein the balance standard depicts a healthy individual with relatively balanced chakras; and determining the baseline relative balance of the subject's energy fields.

3. The method of claim 2 further including repeating steps (a) through (d) until the desired balance against the defined standard of energy fields is achieved.

4. The method of claim 2 further including choosing different external stimuli to find the desired balance for the subject.

5. The method of claim 1, wherein the external stimulus is selected from the group consisting of aroma stimulus, visual stimulus, audio stimulus and touch stimulus.

6. The method of claim 5, wherein the external stimulus is an aroma stimulus.

7. The method of claim 1 wherein the step (c) further comprises reading the subject's corona discharge after exposure to the aroma stimulus at the predetermined intervals for a predetermined period of time.

8. The method of claim 1 wherein the specialized camera is a GDV electrophotography camera.

9. The method of claim 1 wherein the corona images are taken of each fingertip of the subject.

10. The method of claim 1 wherein the quantitative data points representing each reading of the corona discharge of the subject's fingertip are interpreted in terms of parameters selected from the group consisting of area of the image of the corona discharge, intensity of the image of corona discharge and shape of the image of the corona discharge.

11. The method of claim 1 wherein the balance standard is taken for a predetermined period of time of between 5 minutes to 10 days.

12. The method of claim 1 wherein the digitized image of the corona discharge of the subject depicts the energy level around the seven integrated energy centers of the subject.

13. The method of claim 1 wherein the subconscious response to the external stimulus is measured as the subject's adaptation stage to the external stimulus.

* * * * *